United States Patent
Kim

(10) Patent No.: US 11,337,745 B2
(45) Date of Patent: May 24, 2022

(54) DEVICE FOR TREATMENT OF ACNE AND CONTROL METHOD OF THE SAME

(71) Applicant: ILOODA Co., Ltd., Suwon-si (KR)

(72) Inventor: Young Han Kim, Suwon-si (KR)

(73) Assignee: ILOODA Co., Ltd., Suwon-si (KR)

( * ) Notice: Subject to any disclaimer, the term of this patent is extended or adjusted under 35 U.S.C. 154(b) by 976 days.

(21) Appl. No.: 15/990,830

(22) Filed: May 29, 2018

(65) Prior Publication Data

US 2019/0365450 A1 Dec. 5, 2019

(51) Int. Cl.
| | |
|---|---|
| A61B 18/02 | (2006.01) |
| A61B 18/00 | (2006.01) |
| A61B 17/00 | (2006.01) |
| A61K 41/00 | (2020.01) |

(52) U.S. Cl.
CPC .... A61B 18/02 (2013.01); *A61B 2017/00747* (2013.01); *A61B 2018/00452* (2013.01); *A61B 2018/0293* (2013.01); *A61K 41/0052* (2013.01)

(58) Field of Classification Search
CPC ...................................................... A61B 18/02
See application file for complete search history.

(56) References Cited

U.S. PATENT DOCUMENTS

2009/0171334 A1* 7/2009 Elkins ................ A61B 18/02
606/21
2019/0000541 A1* 1/2019 Ko ................... A61B 18/1477

FOREIGN PATENT DOCUMENTS

| KR | 10-1998-0042501 A | 8/1998 |
| KR | 10-2002-0088833 A | 11/2002 |
| KR | 10-0598765 B1 | 7/2006 |

* cited by examiner

*Primary Examiner* — Kaitlyn E Smith
(74) *Attorney, Agent, or Firm* — Revolution IP, PLLC

(57) ABSTRACT

A device for treatment of acne includes: a case having a contact surface portion to contact a skin of an acne region, the contact surface portion being provided with at least one through hole; at least one needle inserted into the skin of the acne region through the through hole with the contact surface portion arranged in contact with the skin; a driving unit arranged inside the case; a needle fixing part arranged inside the case so as to fix the at least one needle and configured to be linearly moved by the driving unit; and a needle cooling unit configured to cooling the at least one needle to transfer coldness into the skin of the acne region through the at least one needle to suppress a function of a sebaceous gland in the skin of the acne region such that proliferation of propionibacterium acnes is limited.

3 Claims, 9 Drawing Sheets

(a)　　　　　　　　　　　(b)

(a)　　　　　　　　　　　(b)

(a)

(b)

(a)          (b)

(a) (b)

(a)          (b)

DEVICE FOR TREATMENT OF ACNE AND CONTROL METHOD OF THE SAME

BACKGROUND

Field of the Invention

The present invention relates to a device for treatment of acne and a control method thereof, and more particularly, to a device for treating acne by inhibiting proliferation of acne bacteria, which grow by secretion of sebaceous glands, by cooling sebaceous glands in the skin and suppressing secretion of sebaceous glands, and a control method thereof.

Description of the Related Art

Acne is a chronic inflammatory disease that develops in the sebaceous glands connected to the follicles, and occurrence of acne is closely related to the function of the sebaceous glands. Acne develops when propionibacterium acnes, which are the cause of acne, proliferate by feeding themselves secretions from sebaceous glands.

FIG. 1 shows the mechanism of occurrence of acne. As the secretion 30 is excessively secreted from a sebaceous gland 20 connected to a side of a follicle 10 in the dermal layer below the epidermis E and keratinization of the skin becomes excessive as shown in FIGS. 1(a) and 1(b), secretions and keratin are accumulated in the sebaceous glands as shown in FIG. 1(c). As a result, the follicle 10 is clogged, the propionibacterium 25 greatly proliferate by feeding on the secretion 30, resulting in inflammation 40. As the propionibacterium acnes 25 significantly proliferate, the inflammation 40 becomes bigger and swollen. Thereby, acne develops.

There are drug treatment and physical therapy for treatment of such acne. In the drug treatment, a retinoid agent for suppressing hyperkeratosis or various other drugs for inhibiting propionibacterium acnes are used. Physical therapy includes a method of suppressing propionibacterium acnes using therapeutic light such as laser and a method of suppressing propionibacterium acnes using high-frequency energy.

However, in the drug treatment, using a drug is temporarily effective in suppressing excessive production of sebum or inhibiting propionibacterium acnes, but it is hardly expected that the effect will be sustained. To obtain a sustained effect, persistent drug treatment is required, which is a burden.

In addition, in the case of the physical therapy, even if propionibacterium acnes are suppressed using laser or high-frequency energy, the propionibacterium acnes will persistently proliferate as long as excessive production of sebum from the sebaceous glands continues. Accordingly, the effect from the therapy is not persistent.

The following documents are published as prior art documents related to conventional acne treatment.

1. Korean Patent Application Publication No. 1998-0042501
2. Korean Patent No. 0598765
3. Korean Patent Application Publication No. 2002-0088833

In recent years, it has been found as a result of research that cryotherapy effectively suppresses the function of the sebaceous glands.

In order to prevent burns on the epidermis of the skin when the laser is radiated into the acne area in treating acne using a laser device, the laser device is provided with a cooling device for cooling the epidermis by spraying a cooling gas on the epidermis of the skin. Thereby, cooling is performed by the cooling device together with treatment with the laser.

In many cases, cooling by the cooling device is more effective than laser treatment in treating acne as it suppresses the function of the sebaceous gland. Thus, it is recognized that cryotherapy is considerably effective in acne treatment.

However, when acne is treated using a cooling device, such as spraying a cooling gas on the epidermis of the skin, there is a risk of inducing more problematic lesions such as hypochromia or hemachromotosis as side effects of cryotherapy.

SUMMARY

Therefore, the present invention has been made in view of the above problems, and it is an object of the present invention to provide an acne treatment device and a control method thereof for implementing acne treatment by cryotherapy for inhibiting proliferation of propionibacterium acnes, which proliferate by feeding on secretions of sebaceous glands, by suppressing the function of the sebaceous glands in the skin to suppress sebaceous secretion of sebaceous glands. Particularly, the present invention provides an acne treatment device and a control method thereof that are capable of further improving the effect of inhibiting the function of the sebaceous glands and proliferation of propionibacterium acnes and minimizing various side effects caused by cooling of skin epidermis by transferring coldness directly to a sebaceous gland which is an object of cryotherapy by inserting at least one needle into the sebaceous gland or a position therearound in the skin.

In accordance with the present invention, the above and other objects can be accomplished by the provision of a device for treatment of acne including a case having a contact surface portion to contact a skin of an acne region, the contact surface portion being provided with at least one through hole, at least one needle inserted into the skin of the acne region through the through hole with the contact surface portion arranged in contact with the skin, a driving unit arranged inside the case, a needle fixing part arranged inside the case so as to fix the at least one needle and configured be linearly moved by the driving unit, and a needle cooling unit configured to cooling the at least one needle to transfer coldness into the skin of the acne region through the at least one needle to suppress a function of a sebaceous gland in the skin of the acne region such that proliferation of propionibacterium acnes is limited.

In accordance with another aspect of the present invention, there is provided a device for treatment of acne including a case having a contact surface portion to contact a skin of an acne region, the contact surface portion being provided with at least one through hole, at least one needle inserted into the skin of the acne region through the through hole with the contact surface portion arranged in contact with the skin, the at least one needle having a hollow channel portion formed therein so as to be hollow, a driving unit arranged inside the case, a needle fixing part arranged inside the case so as to be linearly moved by the driving unit and provided with a gas accommodation portion to accommodate a cooling gas therein, the gas accommodation portion communicating with the hollow channel portion of the at least one needle to fix the at least one needle, and a controller configured to control the driving unit so as to linearly move the needle fixing part such that the at least one needle is inserted into the skin and the cooling gas supplied to the gas accommodation portion is sprayed into the skin through the hollow channel portion of the at least one needle, wherein a function of a sebaceous gland in the skin of the acne region is suppressed by spraying the cooling gas into the skin such that proliferation of propionibacterium acnes is limited.

Preferably, the device may further include a heating portion provided to the contact surface portion to contact and heat the skin or an electrode portion provided to the contact surface portion and configured to generate heat by transmitting high-frequency energy to the contacted skin.

Preferably, the device may further include a temperature sensor provided to the contact surface portion to sense a temperature of the contacted skin, wherein the heat generated by the heating portion or the high-frequency energy applied to the electrode portion may be controlled according to the temperature sensed by the temperature sensor.

Preferably, the device may further include a cooling portion provided to the contact surface portion to contact the skin to take heat away from the contacted skin and cool the skin.

Preferably, the needle cooling unit may include a refrigerant chamber arranged between an inner surface of the contact surface portion inside the case and the needle fixing part so as to be penetrated by the at least one needle and forming therein a space allowing a predetermined refrigerant to flow therethrough, wherein the refrigerant chamber may be provided with a refrigerant inlet portion on one side thereof and a refrigerant outlet portion on an opposite side thereof, wherein the refrigerant inlet portion and the refrigerant outlet portion may be connected to an external refrigerant supply unit such that the refrigerant cools the at least one needle penetrating the refrigerant chamber while flowing into the refrigerant chamber through the refrigerant inlet portion and flowing out to the refrigerant outlet portion according to an operation of the refrigerant supply unit.

Preferably, the at least one needle may include an exposed portion exposed to the refrigerant in the refrigerant chamber as the at least one needle is inserted into the skin, a tip portion exposed to a tissue of the skin, and an insulation portion arranged between the exposed portion and the tip portion to block transfer of coldness to the skin.

Preferably, the needle cooling unit may include a refrigerant space portion provided in the needle fixing part to form a space allowing a predetermined refrigerant to flow therethrough, wherein a portion of the at least one needle may be configured to be exposed to the refrigerant in the refrigerant space portion such that the at least one needle is cooled by the refrigerant, wherein the needle fixing part may be provided, on one side thereof, with a refrigerant inlet portion communicating with one side of the refrigerant space portion and provided, on an opposite side thereof, with a refrigerant outlet portion communicating with an opposite side of the refrigerant space portion, wherein the refrigerant inlet portion and the refrigerant outlet portion may be connected to an external refrigerant supply unit such that the refrigerant cools the at least one needle exposed in the refrigerant space portion while flowing into the refrigerant space portion through the refrigerant inlet portion and flowing out to the refrigerant outlet portion according to an operation of the refrigerant supply unit.

Preferably, the needle fixing part may include a needle fixing body configured to define an accommodation groove therein and fix the at least one needle, and an operation cover coupled to the needle fixing body to seal the accommodation groove to form the gas accommodation portion and configured to be moved with respect to the needle fixing body by the driving unit to compress the gas accommodation portion, wherein, while the needle fixing part is linearly moved and the at least one needle is inserted into the skin as the controller drives the driving unit, the controller may control the cooling gas so as to be supplied to the gas accommodation portion, wherein, while the cooling gas is supplied to the gas accommodation portion, the controller may control the driving unit to cause the operation cover to compress the gas accommodation portion such that the cooling gas in the gas accommodation portion is sprayed into the skin through the hollow channel portion of the at least one needle.

Preferably, the device may further include an elastic support arranged between the needle fixing body and the operation cover to elastically support the operation cover with respect to the needle fixing body.

Preferably, the needle fixing body may include a body bottom portion forming a bottom of the accommodation groove and configured to fix the at least one needle, a guide wall forming a sidewall of the accommodation groove and configured to guide movement of the operation cover, the operation cover being fitted into the guide wall, and a step portion formed on the guide wall to limit a range of the movement of the operation cover caused by the driving unit.

Preferably, the needle fixing body may be provided with an injection groove formed in a part of the body bottom portion to which the at least one needle is fixed, wherein the operation cover may include an injection protrusion protruding from a lower end of the operation cover so as to correspond to the injection groove, the injection protrusion being configured to be fitted into the injection groove to cause the cooling gas to be sprayed through the hollow channel portion of the at least one needle when the operation cover is moved by the driving unit to compress the gas accommodation portion.

In accordance with another aspect of the present invention, there is provided a method of controlling an acne treatment device for treating acne by inserting at least one needle into a skin of an acne region, the method including transferring, through a heating portion or an electrode portion provided to a contact surface portion of a case contacting the skin, heat to the contacted skin, controlling a driving unit arranged inside the case to move a needle fixing part for fixing the at least one needle and causing the at least one needle to be inserted into the skin to which the heat is transferred, wherein the acne treatment device includes a refrigerant chamber arranged between an inner surface of the contact surface portion inside the case and the needle fixing part so as to be penetrated by the at least one needle and forming therein a space allowing a predetermined refrigerant to flow therethrough, and supplying the refrigerant to the refrigerant chamber with the at least one needle inserted into the skin and causing the at least one needle to be cooled by the refrigerant, wherein coldness is transferred into the skin of the acne region through the at least one needle to suppress a function of a sebaceous gland in the skin of the acne region such that proliferation of propionibacterium acnes is limited.

Preferably, the transferring of heat may include sensing a temperature of an epidermis of the skin through a temperature sensor provided to the contact surface portion, transferring heat to the contacted skin through the heating portion or the electrode portion, and blocking the heat transfer through the heating portion or the electrode portion when the temperature sensed by the temperature sensor reaches a preset temperature.

In accordance with a further aspect of the present invention, there is provided a method of controlling an acne treatment device for treating acne by inserting at least one needle into a skin of an acne region, the method including controlling a driving unit arranged inside a case to move a needle fixing part and causing the at least one needle to be inserted into the skin, the needle fixing part being configured to fix the at least one needle having a hollow channel portion formed therein so as to be hollow, controlling an external cooling gas supply unit and causing a predetermined cooling gas to flow from the cooling gas supply unit into a gas accommodation portion formed in the needle fixing part, and controlling the cooling gas supplied from the gas accommodation portion so as to be sprayed into the skin through the hollow channel portion of the at least one needle, wherein a function of a sebaceous gland in the skin of the acne region is suppressed by spraying the cooling gas into the skin such that proliferation of propionibacterium acnes is limited.

Preferably, the needle fixing part may include a needle fixing body configured to define an accommodation groove therein and fix the at least one needle, and an operation cover coupled to the needle fixing body to seal the accommodation groove to form the gas accommodation portion and configured to be moved with respect to the needle fixing body by the driving unit to compress the gas accommodation portion, wherein the controlling of the cooling gas so as to be sprayed may include causing, while the at least one needle is inserted into the skin by moving the needle fixing part by controlling the driving unit and the cooling gas is supplied into the gas accommodation portion, the operation cover to compress the gas accommodation portion by re-controlling the driving unit and causing the cooling gas of the gas accommodation portion to be sprayed into the skin through the hollow channel portion of the at least one needle.

Preferably, the method may further include controlling, before the at least one needle is inserted into the skin, the heat so as to be transferred to the contacted skin through the heating portion or the electrode portion provided to the contact surface portion of the case contacting the skin such that an epidermis tissue of the skin is not damaged by coldness of the needle.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Reference will now be made in detail to the preferred embodiments of the present invention, examples of which are illustrated in the accompanying drawings. Wherever possible, the same reference numbers will be used throughout the drawings to refer to the same or like parts.

An acne treatment device and a control method thereof according to the present invention will be described in more detail with reference to the accompanying drawings. First, the configuration and control system of an acne treatment device according to an embodiment of the present invention will be described with reference to FIG. 2.

Figure 1:
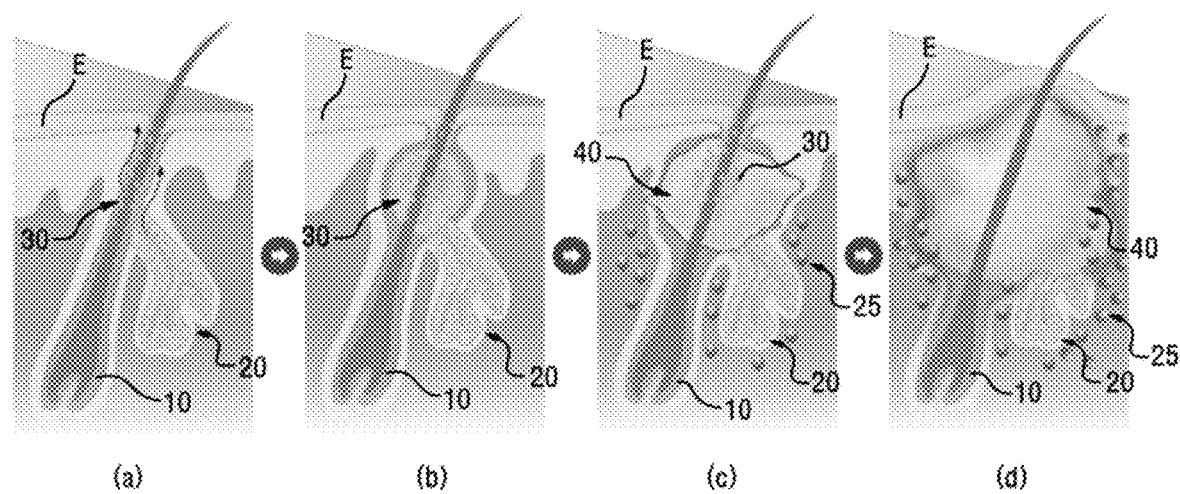
FIG. 1 shows a typical mechanism of occurrence of acne.
Figure 2:
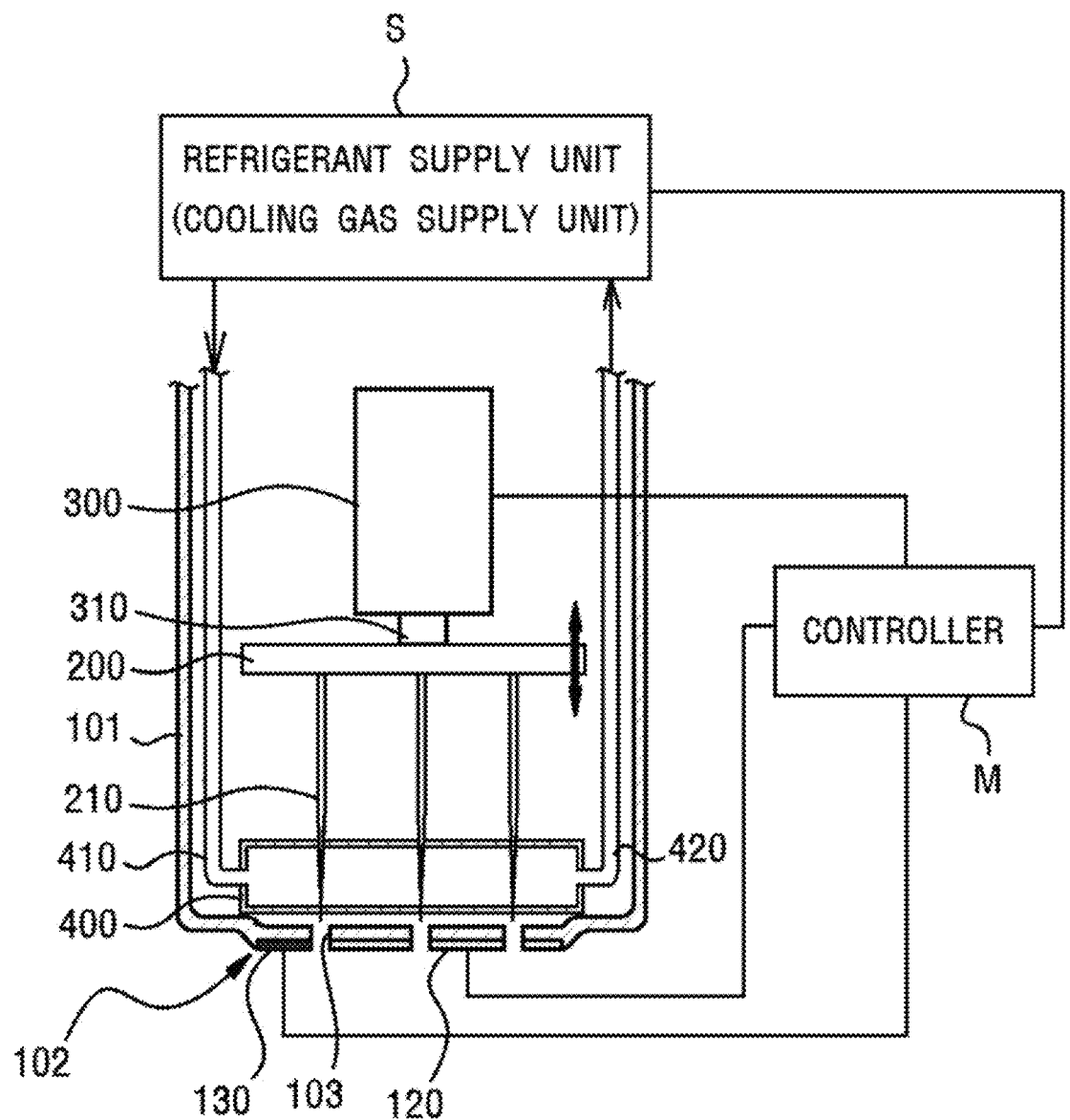
FIG. 2 is a view illustrating a configuration and a control system of an acne treatment device according to an embodiment of the present invention.

As shown in FIG. 2, the acne treatment device according to an embodiment of the present invention includes a needle fixing unit 200 for fixing at least one needle 210, a driving unit 300 for driving the needle fixing part 200, and a needle cooling unit, all of which are provided inside a case 101.

In treating acne produced on the skin of a subject, the therapist brings a contact surface portion 102 formed at an end of the case 101 of the acne treatment device according to the present invention into contact with the skin of the acne area of the subject.

As shown in FIG. 2, the actuator 310 of the driving unit 300 is fixed to the needle fixing part 200 and at least one needle 210 is fixed to the needle fixing part 200. A through hole 103 corresponding to the at least one needle 210 is formed in the contact surface portion 102. Thus, when the driving unit 300 moves the needle fixing part 200 by driving the actuator 310, the at least one needle 210 fixed to the needle fixing part 200 protrudes through the through hole 103 is and is inserted into the skin.

The needle cooling unit cools the at least one needle 210 such that the coldness is transferred to the vicinity of the position of the sebaceous gland when the at least one needle 210 is inserted into the skin. FIG. 2 shows a refrigerant chamber 400 as an example of the needle cooling unit.

As shown in FIG. 2, the needle cooling unit may include a refrigerant chamber 400 arranged between the inner surface of the contact surface portion 102 inside the case 101 and the needle fixing part 200 and defining therein a space through which a predetermined refrigerant flows.

Preferably, the at least one needle 210 is configured to penetrate the refrigerant chamber 400.

That is, when the needle fixing part 200 is moved by driving of the driving unit 300 and the needle 210 is inserted into the skin, the needle 210 is arranged through the refrigerant chamber 400. Thus, the needle 210 is moved and inserted into the skin while penetrating the refrigerant chamber 400.

Although not specifically shown in the figure, a portion of the needle 210 penetrating the refrigerant chamber 400 preferably further includes an element capable of maintaining the refrigerant chamber 400 in a sealed state such that the refrigerant in the refrigerant chamber 400 does not flow out through the portion of the needle 210 penetrating the refrigerant chamber 400. That is, a member to maintain the refrigerant chamber 400 in a sealed state to prevent the refrigerant of the refrigerant chamber 400 from flowing out while the needle 210 arranged through the refrigerant chamber 400 is allowed to freely move rectilinearly may be provided to the penetrating portion of the needle 210.

As shown in FIG. 2, a refrigerant inlet portion 410 is provided on one side of the refrigerant chamber 400 and a refrigerant outlet portion 420 is provided on the other side of the refrigerant chamber 400. Preferably, the refrigerant inlet portion 410 and the refrigerant outlet portion 420 are connected to an external refrigerant supply unit S such that the refrigerant cools the at least one needle 210 penetrating the refrigerant chamber 400 while flowing into the refrigerant chamber 400 through the refrigerant inlet portion 410 and flowing out through the refrigerant outlet portion 420 according to operation of the refrigerant supply unit S.

Here, the refrigerant supply unit S may be an apparatus that supplies a predetermined refrigerant at a low temperature by refrigerating the refrigerant by a refrigeration cycle for the refrigerant, or may be an apparatus including a storage for compressing and storing a predetermined refrigerant and a control valve for controlling supply of the refrigerant stored in the storage.

The refrigerant may be any material that can be cooled to a low temperature by a refrigeration cycle. It may be a liquefied gas or a cooling gas such as carbon dioxide which is not harmful to the human body.

The present invention includes both an embodiment in which the needle is cooled by exposing the needle to the refrigerant so as to transfer coldness to the skin tissue in a radiative manner and an embodiment in which the needle has a hollow channel portion such that the cooling gas is directly sprayed onto the skin tissue. When the needle is used only for the purpose of cooling, the cooling gas may be used in the refrigerant supply unit and any type of refrigerant other than the cooling gas may also be used. On the other hand, when the needle is used to spray a cooling gas, the refrigerant supply unit should supply a cooling gas, such as a carbonic acid gas, which is not harmful to the human body. In this case, the refrigerant supply unit is referred to as a cooling gas supply unit.

The refrigerant supply unit and the cooling gas supply unit are the same, and the kind of refrigerant may vary among the embodiments.

The driving unit 300 may have substantially the same configuration as a driving unit used in a handpiece of a medical instrument using a needle.

All subsequent drawings including FIG. 2 show a driving unit configured to drive the actuator by way of example.

That is, the actuator 310 may be configured in the form of a lead screw, a ball screw, or the like, and a motor (which may be a typical motor or a stepper motor) in the driving unit 300 may rotate to drive the actuator 310 such as the lead screw or the ball screw in a linear direction.

Of course, the driving unit may be implemented in the form of a hydraulic cylinder, a solenoid, or the like. In order to accurately and precisely control the stroke distance of the needle fixing part, a stepper motor or the like is preferably employed to precisely drive the actuator such as the lead screw or the ball screw.

As mentioned above, the epidermis of the skin may suffer side effects such as hypochromia or hemachromotosis due to the cooling operation in the cryotherapy process. Therefore, in cryotherapy using cooling of the needle as described above, it is necessary to eliminate side effects that may occur when the cooled needle contacts the epidermis of the skin.

For example, there may be a need for a separate method to inhibit transfer of heat from the epidermis of the skin before or at the same time as the cooling treatment using the needle, depending on the condition and sensitivity of the skin of the subject.

In order to prevent the epidermis of the skin from being cooled down, the acne treatment device according to an embodiment of the present invention may include a heating portion or an electrode portion 120 in the contact surface portion 102 configured to contact the skin as shown in FIG. 2. Thus, heat may be generated by applying heat to the epidermis of the skin through the heating portion or transmitting high-frequency energy to the skin through the electrode portion contacting the skin.

That is, by performing protective heating of applying appropriate heat to the epidermis of the skin through the heating portion or the electrode portion 120 and then conducting cryotherapy using the needle, the skin epidermis may be protected from the coldness, and side effects from the cryotherapy may be prevented.

For example, the heating portion may be implemented by providing a hot wire or the like to the contact surface portion 102. The electrode portion may be connected to an energy source for transmitting electromagnetic waves of a high frequency and a current may be applied thereto. Thereby, high-frequency energy may be transmitted via the electrode portion.

More preferably, a temperature sensor 130 is provided on one side of the contact surface portion 102 to sense the temperature of the skin contacting the contact surface portion 102 and to control the heat generated from the heating portion 120 or the high-frequency energy applied to the electrode portion 120 according to the sensed temperature. Thereby, appropriate protective heating may be performed on the epidermis of the skin.

Preferably, the operation of the driving unit 300, the operation of the refrigerant supply unit S, recognition of the temperature sensed by the temperature sensor 130, and the operation of the heating portion or the electrode portion 120 are all controlled by the controller M, as shown in FIG. 2.

The operation of the acne treatment device according to various embodiments of the present invention having the configuration and the control system as shown in FIG. 2 will be described in more detail with reference to FIGS. 3 to 9.

In the following discussion of FIGS. 3 to 9, description of the controller M and components connected thereto will be omitted. Although not separately shown, it is basically assumed that the operation of the driving unit 300, the operation of the refrigerant supply unit S, and recognition of the temperature sensed by the temperature sensor 130, and the operation of the heating portion or electrode portion 120 are controlled by the controller M.

First, the operation and control of an acne treatment device according to an embodiment of the present invention will be described with reference to FIG. 3. Among the elements of the acne treatment device shown in FIG. 3, the same elements as described with reference to FIG. 2 will not be described in detail.

FIGS. 3(a), 3(d) and FIGS. 4(a) and 4(b) sequentially illustrate the process of acne treatment using an acne treatment device according to an embodiment of the present invention.

As shown in FIG. 3(a), the therapist is required to be aware of information about the depth of a target region T in the vicinity of a sebaceous gland which needs to be cooled in the dermis D of the skin at the portion of acne to be treated.

The depth of insertion of the needle 210 is determined according to the depth of the target area T. Accordingly, treatment needs to be prepared for by controlling the driving range of the driving unit 300 or installing a needle fixing part having a needle having an appropriate length corresponding to the insertion depth.

As shown in FIG. 3(b), in order to treat acne, the controller causes protective heating to be performed on the epidermis E of the skin through the heating portion or electrode portion 120 with the contact surface portion 102 of the case 101 contacting a skin portion. Reference numeral HR represents a portion of the skin epidermis E subjected to protective heating in FIG. 4(a). Hereinafter, this portion will be referred to as a "heated region".

Figure 4:
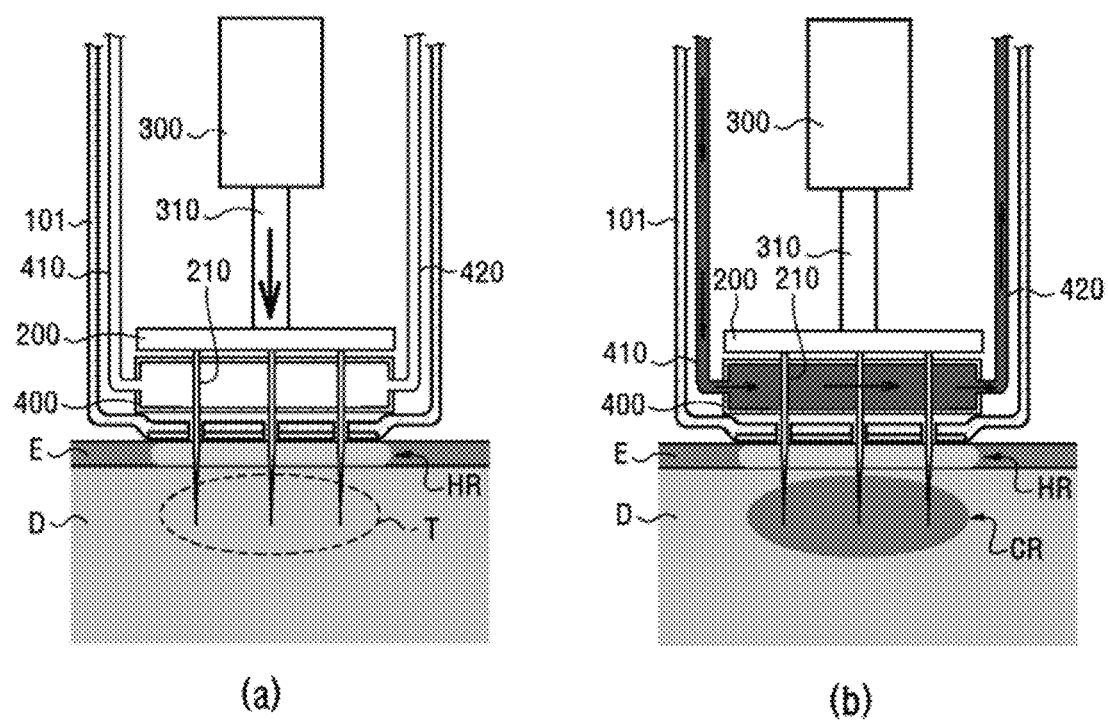

After the heated region HR is formed by appropriate protective heating on the epidermis E of the skin by the heating portion or electrode portion 120, the controller controls the driving portion 300 as shown in FIG. 4(*b*). Thereby, the actuator 310 is linearly driven in a longitudinal direction to move the needle fixing part 200 coupled to the end of the actuator 310 such that at least one needle 210 fixed to the needle fixing part 200 is inserted into the target region T in the dermis D of the skin.

At this time, the needle 210 is moved and inserted into the skin by the needle fixing part 200 with the refrigerant chamber 400 penetrated by the needle 210, and the upper portion of the needle 210 is exposed to the interior of the refrigerant chamber 400 by movement of the needle 210. Here, the needle 210 is made of a predetermined metal material having very high thermal conductivity.

After the needle 210 is inserted into the target region T in the skin, the controller drives the refrigerant supply unit S (see FIG. 2) as shown in FIG. 4(*b*) to cause a predetermined refrigerant to be introduced into the refrigerant chamber 400 through the refrigerant inlet portion 410, and the introduced refrigerant flows out through the refrigerant outlet portion 420 by the pressure thereof and is thus recovered or discharged to the outside.

As the refrigerant is introduced into the refrigerant chamber 400 and the portion of the needle 210 is cooled through the portion of the needle 210 exposed to the interior of the refrigerant chamber 400, the needle 210 delivers the coldness to the target region T and thus a cooled region CR is created as shown in FIG. 4(*b*). As the cooled region CR is created, the sebaceous gland is directly and indirectly cooled and thus the function thereof is suppressed.

As the function of the sebaceous gland is suppressed by cooling, production of sebum in the sebaceous gland is suppressed, and thus propionibacterium acnes that grow by secretion of sebaceous gland are necrotized. Thereby, acne is treated.

That is, as the needle 210 is inserted and is cooled through the refrigerant and coldness is transferred to the target region after the heated region HR is formed by protective heating on the epidermis E of the skin, coldness may be directly transferred to the target region to conduct cryotherapy without damaging the epidermis E of the skin by cooling. Accordingly, acne may be treated very effectively and stably.

Figure 3:
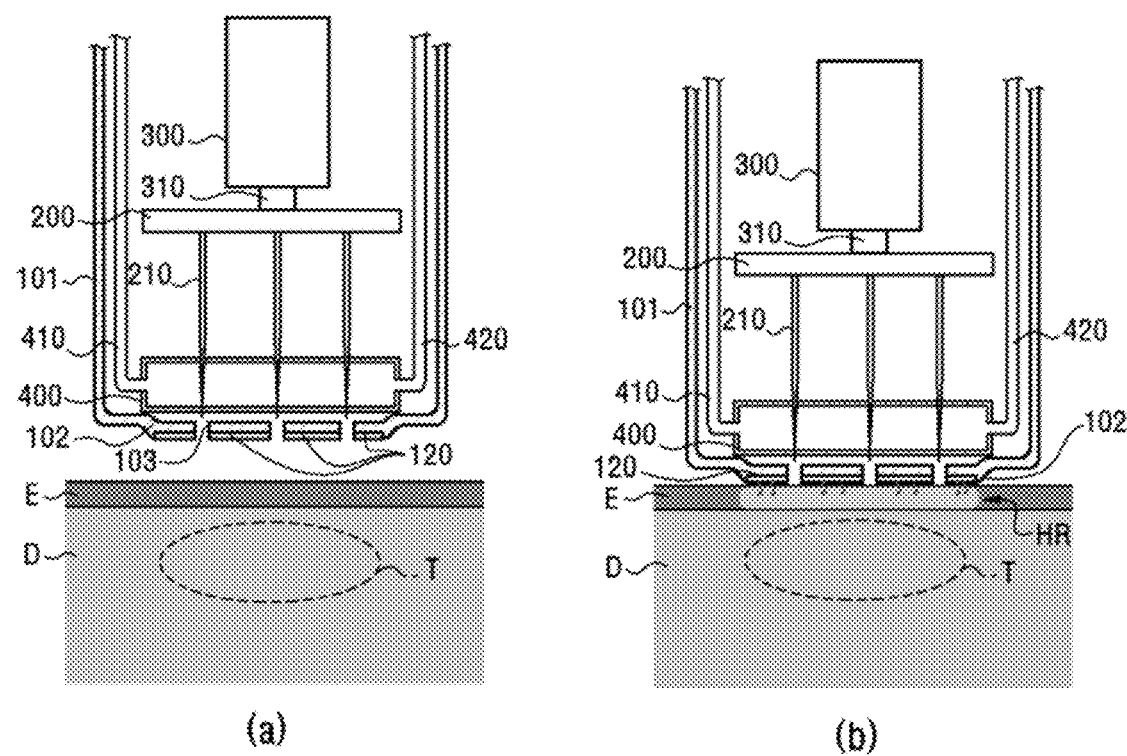
FIG. 3 and FIG. 4 sequentially illustrate the process of acne treatment using an acne treatment device according to an embodiment of the present invention.

In the cryotherapy performed on a portion near a sebaceous gland by cooling the needle as described above, forming the heated region HR for the epidermis E of the skin as shown in FIG. 3(*b*) may lower the efficiency of transfer of coldness to the target region T.

That is, since the needle 210 is formed of a metal material having a high thermal conductivity, it is affected by the refrigerant, and heat of the heated region HR may be transferred to the needle 210. As a result, the temperature of the coldness transferred to the target region T through the needle 210 may be higher than a target temperature.

For example, while the target region T should be cooled to −30° C. through the needle 210, it may be set at a higher temperature due to heat transferred from the heated region HR to the needle 210. In this case, the effect of cryotherapy on the sebaceous glands may be deteriorated.

Therefore, in some cases, protective heating on the epidermis E as shown in FIG. 3(*b*) is preferably omitted, and cooling of the needle and transfer of coldness are preferably performed by the refrigerant as shown in FIGS. 4(*a*) and 4(*b*).

Further, it may be more preferable that the contact portion 102 be provided with a cooling portion (not shown) in place of the heating portion or electrode portion 120 (for example, a thermoelectric element or an element thermally connected to the refrigerant chamber may be used to cool the portion contacting the skin) such that the epidermis is pre-cooled to a certain extent before insertion of the needle and then coldness is transferred through the needle.

Figure 5:
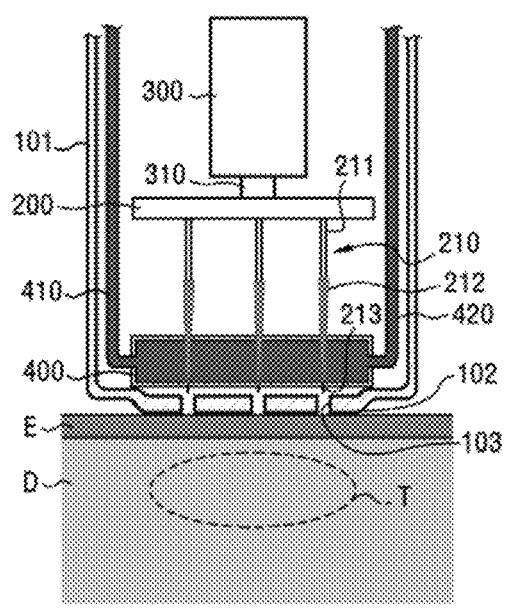
FIG. 5 sequentially illustrate the process of acne treatment using an acne treatment device according to another embodiment of the present invention.
Figure 5:
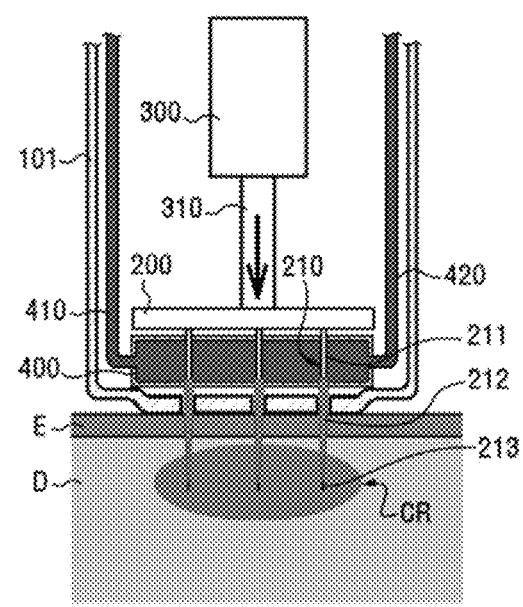

FIG. 5 shows the configuration and the operation of an acne treatment device according to another embodiment of the present invention, which is capable of reducing damage caused by cooling of the epidermis E of the skin without performing protective heating on the epidermis E of the skin.

As shown in FIGS. 5(*a*) and 5(*b*), in the acne treatment device according to this embodiment, the contact surface portion 102 is not provided with the heating portion or the electrode portion 120, but an insulation portion 212 is provided to the needle 210.

The insulation portion 212 provided to the needle 210 may be formed by coating an insulation material or by coating the needle with a protective film of an insulation material.

That is, as shown in FIGS. 5(*a*) and 5(*b*), the needle 210 is configured to have an exposed portion 211 exposed to the refrigerant, an insulation portion 212, and a tip portion 213 exposed to the skin.

As shown in FIG. 5(*a*), before the needle 210 is inserted into the skin, the controller drives the refrigerant supply unit S (see FIG. 2) in advance to supply the refrigerant into the refrigerant chamber 400 through the refrigerant inlet portion 410. The controller drives the driving unit 300 to move the needle fixing part 200 such that the needle 210 is inserted into the target region T in the dermis D of the skin as shown in FIG. 5(*b*).

As shown in FIG. 5(*b*), once the needle 210 is arranged inserted, the exposed portion 211 of the needle 210 is cooled as it is exposed to the refrigerant in the refrigerant chamber 400. The coldness is transferred to the target region at the tip portion 213 by the cooling operation. Since the exposed portion 211 and the tip portion 213 are insulated by the insulation portion 212, coldness of the needle 210 may be obstructed from being well transferred to the skin part which is brought into contact with the insulation portion 212 of the needle 210. Accordingly, the adverse effect that transfer of coldness has on the skin part may be reduced.

In FIGS. 5(*a*) and 5(*b*), cryotherapy is illustrated as being conducted using direct insertion of the needle and transfer of coldness without heating the epidermis of the skin as the heating portion or electrode portion is omitted from the contact surface portion. Since the insulation portion 212 of the needle 210 not only reduces transfer of coldness from the needle to the skin but also can reduce transfer of heat from the skin to the needle, it is also possible in the embodiment illustrated in FIGS. 5(*a*) and 5(*b*) to transfer coldness to the target region by inserting a needle after a heated region is formed by heating the epidermis of the skin using the heating portion or electrode portion (see FIGS. 3 and 4) provided to the contact surface portion 102.

Since all features of the operation illustrated in FIGS. 5(*a*) and 5(*b*) except the configuration of the insulation portion of the needle are the same as those described with reference to FIGS. 3 and 4, a detailed description thereof will be omitted.

Hereinafter, a configuration and operation of an acne treatment device according to another embodiment of the present invention will be described with reference to FIG. 6.

Figure 6:
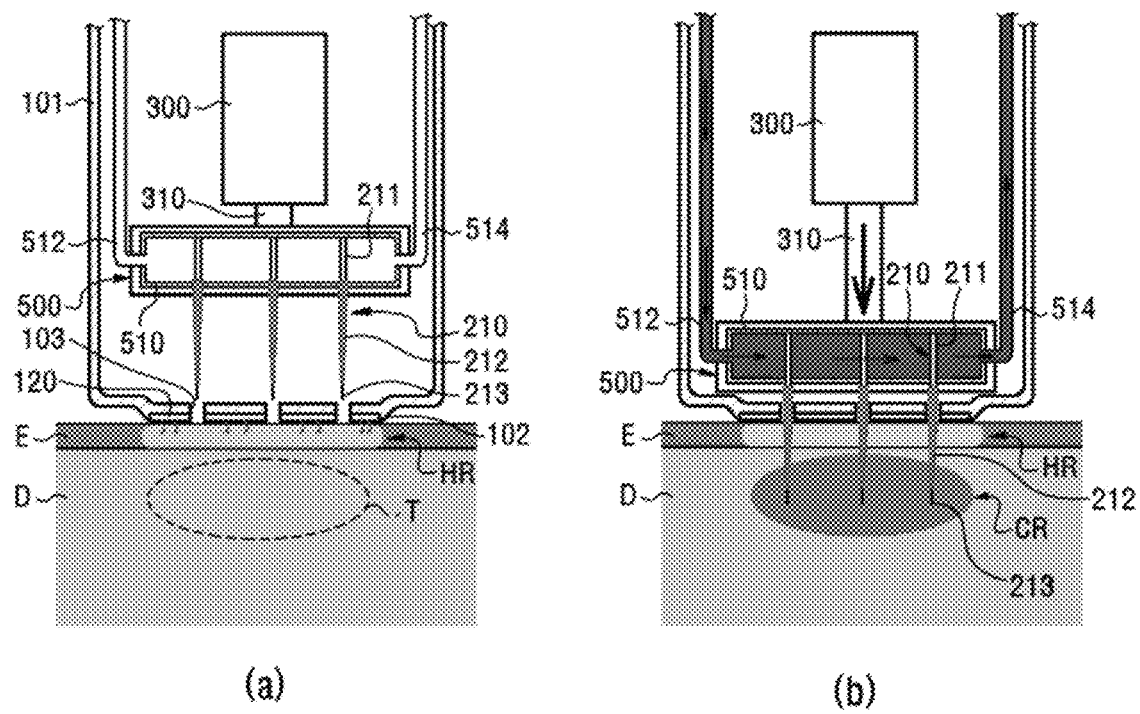
FIG. 6 sequentially illustrate the process of acne treatment using an acne treatment device according to yet another embodiment of the present invention.

In the embodiment illustrated in FIGS. 6(*a*) and 6(*b*), the refrigerant chamber is omitted. Instead, a refrigerant space portion 510 connected to the refrigerant supply unit (not shown) and defining a space through which the refrigerant flows is provided in the needle fixing part 500.

The needle 210 is fixed to the needle fixing part 500. Preferably, the needle 210 is fixed such that the exposed portion 211 of the needle 210 is exposed to the refrigerant space portion 510. The part of the needle 210 except the tip portion 213 and the exposed portion 211 may be provided with the insulation portion 212 formed by insulation coating or the like.

As shown in FIG. 6(*a*), after the heated region HR is created by heating the epidermis E of the skin through the heating portion or electrode portion 120 provided to the contact surface portion 102, the controller drives the driving unit 300 to linearly move the needle fixing part 500 such that the needle 210 is inserted into the target region T in the dermis D of the skin. Then, as shown in FIG. 6(*b*), the refrigerant is supplied into the refrigerant space portion 510 in the needle fixing part 500 through the refrigerant inlet portion 512 by the refrigerant supply unit S (see FIG. 2), and the refrigerant supplied to the refrigerant space portion 510 flows out through the refrigerant outlet portion 514 and is recovered or discharged to the outside.

As the refrigerant flows in the refrigerant space portion 510 in the needle fixing part 500, the exposed portion 211 of the needle 210 is exposed to the refrigerant to be cooled, and the coldness created by the cooling is transferred to the tip portion 213 and is thus transferred to the target region through the tip portion 213 of the needle 210. Thereby, a cooled region CR is created.

In this embodiment, the heated region HR for the epidermis E of the skin may lower the transfer efficiency of coldness of the needle 210. In some cases, the contact portion 102 may not be provided with the heating portion or electrode portion 120 and coldness may be directly transferred into the skin using the needle without protective heating of the epidermis of the skin.

Hereinafter, the configuration and control of an acne treatment device according to another embodiment of the present invention and the corresponding operation thereof will be described with reference to FIGS. 7, 8 and 9.

Figure 7:
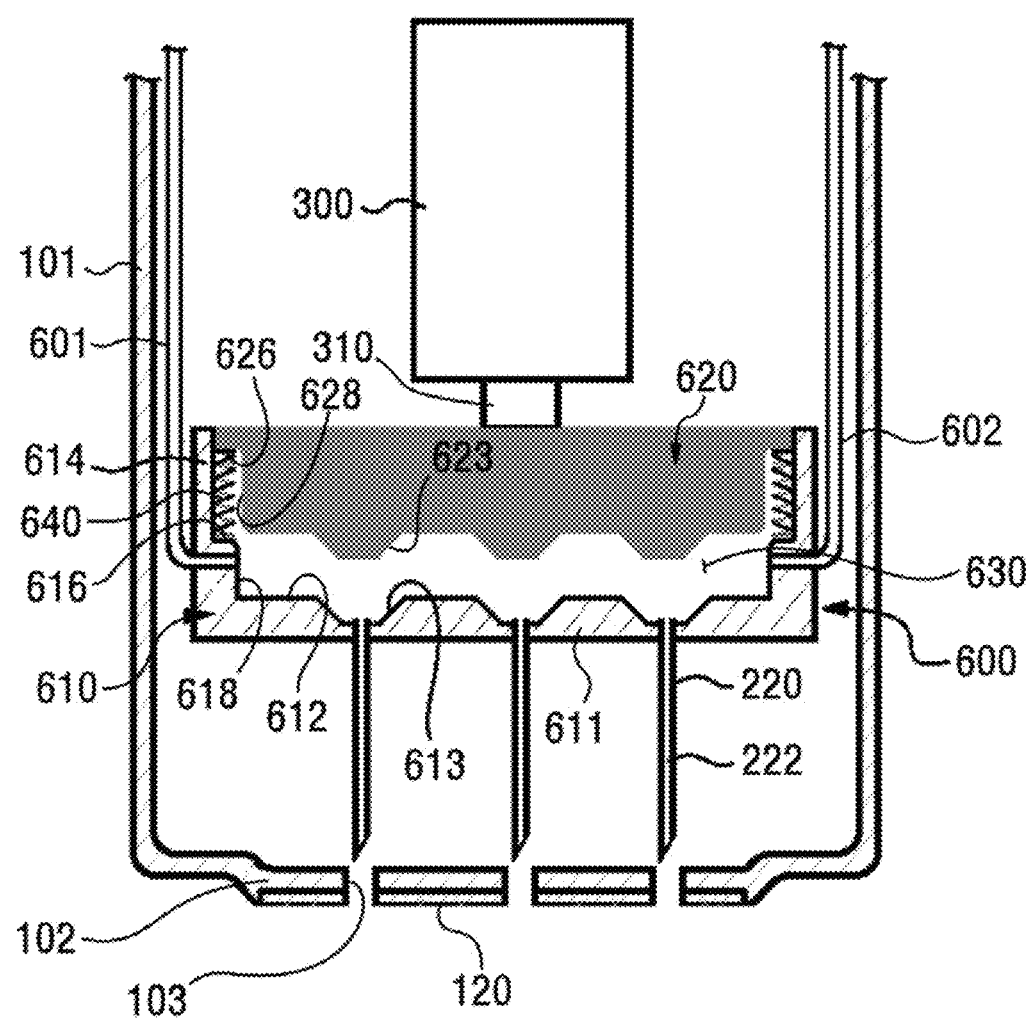
FIG. 7 is a view illustrating a configuration of an acne treatment device according to another embodiment of the present invention.
Figure 8:
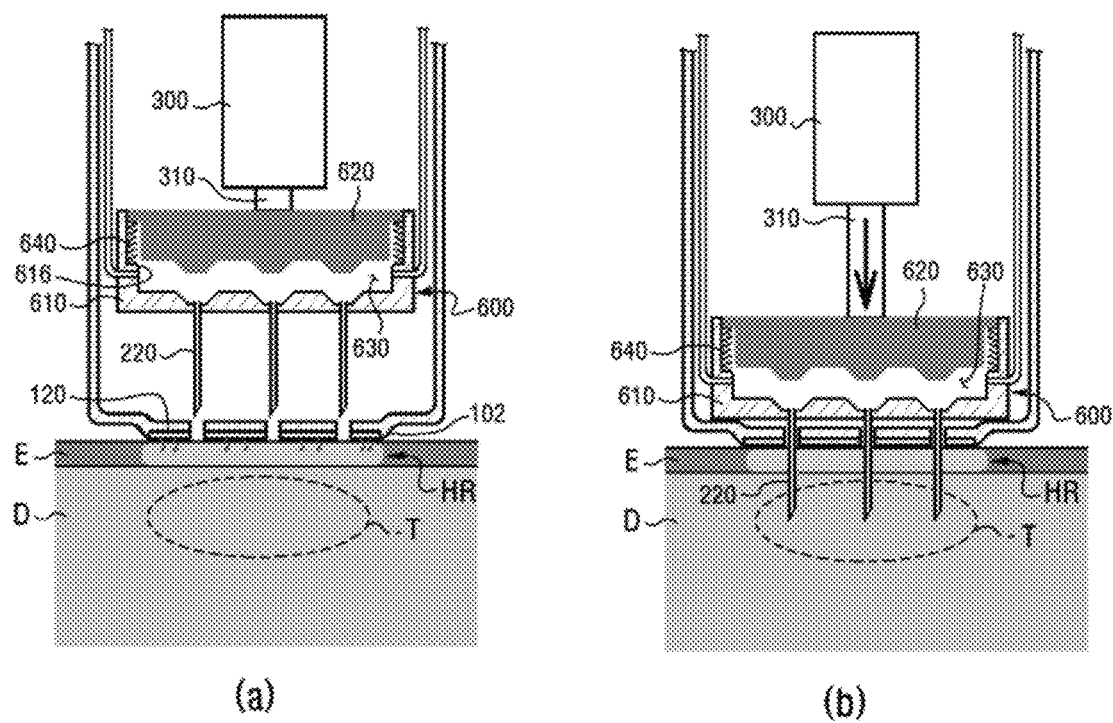
FIG. 8 and FIG. 9 sequentially illustrate control of operation of a main part in the process of acne treatment using the acne treatment device shown in FIG. 6.
Figure 9:
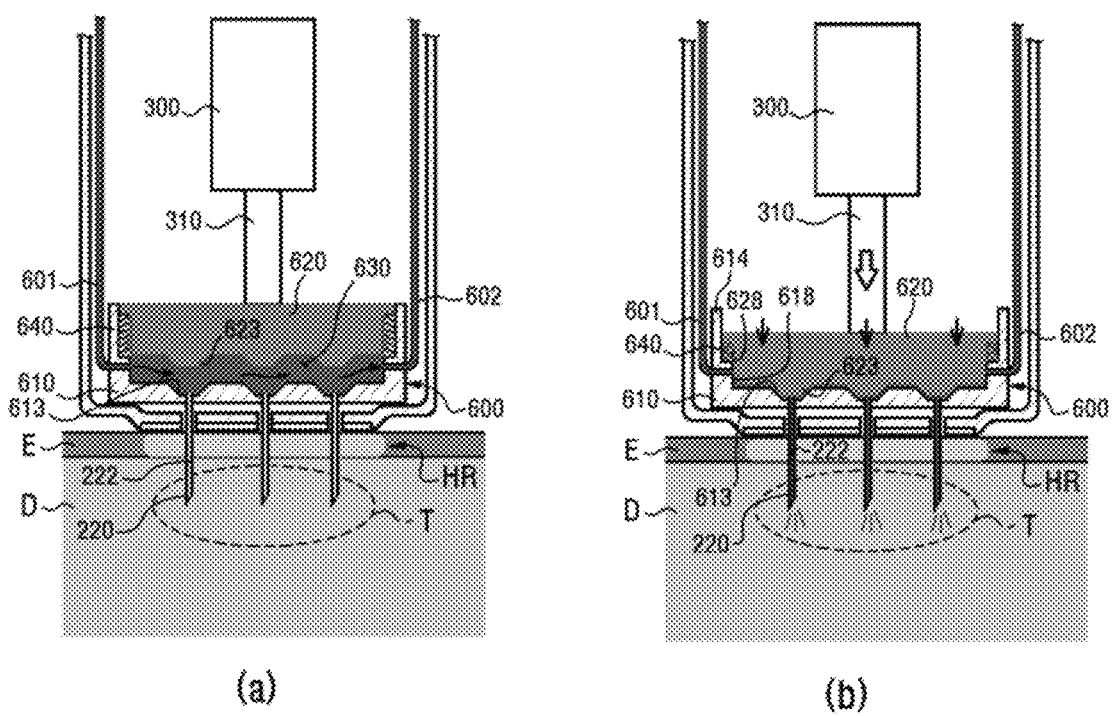

FIG. 7 is a view illustrating a configuration of an acne treatment device according to another embodiment of the present invention, and FIGS. 8 and 9 sequentially illustrate control of operation of a main part in the process of acne treatment using the acne treatment device shown in FIG. 7.

As shown in FIG. 7, the acne treatment device according to this embodiment is basically configured such that the needle sprays a cooling gas directly into a skin tissue.

That is, the needle 220 basically has a hollow channel portion 222 formed to be hollow to allow the cooling gas to flow therethrough.

As shown in FIG. 7, the acne treatment device according to this embodiment includes a penetrating hole 103 formed in the contact surface portion 102 of the case 101 and a heating portion or electrode portion 120 formed on a part of the acne treatment device contacting the skin. As described with reference to FIGS. 3 to 6, the needle 220 is inserted into the skin as the needle fixing part 600 is moved by the driving unit 300 and the actuator 310.

The acne treatment device according to this embodiment is different from the other embodiments in configurations of the needle 220 and the needle fixing part 600.

As shown in FIG. 7, the needle fixing part 600 of the acne treatment device according to this embodiment includes a gas accommodation portion 630 for accommodating a cooling gas therein, and serves to fix at least one needle 220 with the hollow channel portion 222 of the needle 220 arranged in communication with the gas accommodation portion 630.

As shown in FIG. 7, the needle fixing part 600 includes a needle fixing body 610 and an operation cover 620. After the entirety of the needle fixing part 600 is moved by linearly moving the actuator 310 through operation of the driving unit 300, the cooling gas is supplied to the gas accommodation portion 630 in the needle fixing part 600. Then, the controller drives the driving unit 300 again such that the actuator 310 is further extended to push the operation cover 620 to spray the cooling gas contained in the gas accommodation portion 630 through the hollow channel portion 222 of the needle 220.

The needle fixing body 610 is provided therein with an accommodation groove 612 and is configured to fix the at least one needle 220. The operation cover 620 is coupled to the needle fixing body 610 to seal the accommodation groove 612 to form the gas accommodation portion 630 and is moved with respect to the needle fixing body 610 by the driving unit 300 to compress the gas accommodation portion 630.

As such, as the controller controls the driving unit 300, the needle fixing part 600 is linearly moved and the at least one needle 220 is inserted into the skin. In this state, the controller performs a control operation to supply the cooling gas to the gas accommodation unit 630 (namely, it controls the cooling gas supply unit S (see FIG. 2). With the cooling gas supplied to the gas accommodation portion 630, the controller controls the driving unit 300 again to push the operation cover 620 to compress the gas accommodation portion 630. Thereby, the cooling gas in the gas accommodation portion 630 is sprayed into the skin through the hollow channel portion 222 of the needle 220 inserted into the skin.

As shown in FIG. 7, the needle fixing body 610 may include a body bottom portion 611 for defining the bottom of the accommodation groove 612 and fixing the at least one needle 220, a guide wall 614 for defining a sidewall of the accommodation groove 612 and guiding movement of the operation cover 620, the operation cover 620 being fitted into the guide wall 614, a step portion 616 formed on the guide wall 614 to limit the range of movement of the operation cover 620 caused by the driving unit 300.

The flange portion 626 of the operation cover 620 is fitted into the guide wall 614 of the needle fixing body 610 so as to be movable along the guide wall 614. Here, a slide portion 628 formed in a stepped manner is provided below the flange portion 626 of the operation cover 620, and a sidewall portion 618 is formed to connect the step portion 616 of the needle fixing body 610 and the body bottom portion 611. Thus, as the operation cover 620 is pushed by the driving unit 300, the slide portion 628 may be fitted into the sidewall portion 618 and caused to slide. Thereby, the operation cover 620 may compress the gas accommodation portion 630.

Preferably, an elastic support 640, such as a spring, for elastically supporting the operation cover 620 on the needle fixing body 610 may be arranged between the needle fixing body 610 and the operation cover 620.

More specifically, the elastic support 640 may be arranged between the step portion 616 of the needle fixing body 610 and the flange portion 626 of the operation cover 620. The operation cover 620 may be elastically supported on the needle fixing body 610 by the elastic support 640. Therefore, when the driving unit 300 moves the entirety of the needle fixing part 600, the needle 220 may be inserted into the skin by movement of the needle fixing part 600 while the operation cover 620 does not compress the gas accommodation portion 630.

The needle fixing body 610 may be configured to have an injection groove 613 at a position where the needle 220 is fixed to the body bottom portion 611, and an injection protrusion 623 corresponding to the injection groove 613 may be formed at a lower end of the operation cover 620. Thus, when the operation cover 620 is moved by the driving unit 300 to compress the gas accommodation portion 630, the injection protrusion 623 may be fitted into the injection groove 613, and the cooling gas in the gas accommodation portion 630 may be effectively sprayed from the end of the needle 220 through the hollow channel portion 222 of the needle 220.

At this time, an end of the gas inlet portion 601 for introducing the cooling gas from the cooling gas supply unit (not shown) into the gas accommodation portion 630 and an end of the gas outlet portion 602 are formed in the sidewall portion 618 of the needle fixing body 610. When the operation cover 620 is operated by the driving unit 300 to compress the gas accommodation portion 630, the slide portion 628 is fitted into the sidewall portion 618 and slides. Thus, the slide portion 628 may block the end of the gas inlet portion 601 and the end of the gas outlet portion 602, and thus the cooling gas in the gas accommodation portion 630 may be effectively sprayed through the hollow channel portion 222 of the needle 222.

Hereinafter, the operation of the acne treatment device according to this embodiment configured as above will be described with reference to FIGS. 8 and 9.

As shown in FIG. 8(*a*), in order to treat acne, the controller may cause protective heating to be performed on the epidermis E of the skin through the heating portion or electrode portion 120 with the contact surface portion 102 of the case 101 contacting a skin portion.

After the heated region HR is formed by appropriate protective heating of the epidermis E of the skin through the heating portion or electrode portion 120, the controller controls the driving unit 300 and the actuator 310 is linearly driven in the longitudinal direction to move the needle fixing part 600 coupled to an end of the actuator 310 such that at least one needle 220 fixed to the needle fixing part 600 is inserted into the target region T in the dermis D of the skin, as shown in FIG. 8(*b*).

When the driving unit 300 moves the needle fixing part 600, repulsive force is generated according to insertion of the needle 220 into the skin. However, the operation cover 620 may be substantially steadily moved without making a movement with respect to the needle fixing body 610 since the elastic support 640 supports the needle fixing body 610 and the operation cover 620.

After the needle 220 is inserted into the target region T in the skin, the controller drives the cooling gas supply unit S (see FIG. 2) such that a predetermined cooling gas is supplied into the gas accommodation portion 630 in the needle fixing part 600 through the gas inlet portion 601, as shown in FIG. 9(*a*). The cooling gas supplied to the gas accommodation portion 630 flows out through the gas outlet portion 602 and is recovered or discharged to the outside.

Once the cooling gas is supplied to the gas accommodation portion 630 in the needle fixing part 600 as described above, the controller controls the driving unit 300 to further extend the actuator 310 from the current position to apply pressure to the operation cover 620, as shown in FIG. 9(*b*).

As shown in FIG. 9(*b*), the operation cover 620 is moved by the driving unit 300 and the slide portion 628 is fitted into the sidewall portion 618 of the needle fixing body 610 and slides. Thus, the slide portion 628 compresses the gas accommodation portion 630 while blocking the end of the gas inlet portion 601 and the end of the gas outlet portion 602. As compression is performed, the injection protrusion 623 is fitted into the injection groove 613 in the vicinity of a portion to which the needle 220 is fixed, and the cooling gas in the gas accommodation portion 630 is sprayed onto the target region T in the skin through the hollow channel portion 222 of the needle 220.

As the cooling gas is sprayed onto the target region in the skin as described above, the target region is cooled. In addition, the sebaceous gland present in the target region is cooled by the cooling gas and thus the function thereof is inhibited. Thereby, secretion of the sebaceous glands is suppressed, and proliferation of propionibacterium acnes is effectively suppressed. Thereby, acne is treated.

In this embodiment, since the cooling gas is directly sprayed into the target region T without loss of coldness while the heated region HR formed by heating the skin epidermis protects the skin epidermis E, acne cryotherapy may be conducted through more effective cooling of the sebaceous glands.

As is apparent from the above description, the acne treatment device and control method thereof according to the present invention may implement acne treatment by cryotherapy for inhibiting proliferation of propionibacterium acnes, which proliferate by feeding on secretion of sebaceous glands, by suppressing the function of the sebaceous glands in the skin to suppress sebaceous secretion of the sebaceous glands. Specifically, the effect of inhibiting the function of sebaceous glands and proliferation of propionibacterium acnes can be further improved and various side effects caused by cooling of skin epidermis can be minimized by transferring coldness directly to the sebaceous gland which is an object of cryotherapy by inserting at least one needle into the sebaceous gland or a position therearound in the skin.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for treatment of acne comprising:
   a case having a contact surface portion to contact a skin of an acne region, the contact surface portion being provided with at least one through hole;
   at least one needle configured to be inserted into the skin of the acne region through the through hole with the contact surface portion arranged in contact with the skin;
   a driving unit arranged inside the case;
   a needle fixing part arranged inside the case so as to fix the at least one needle and configured to be linearly moved by the driving unit; and
   a needle cooling unit configured to cool the at least one needle to transfer coldness into the skin of the acne region through the at least one needle to suppress a function of a sebaceous gland in the skin of the acne region such that proliferation of propionibacterium acnes is limited,
   wherein the needle cooling unit comprises:
   a refrigerant chamber arranged between an inner surface of the contact surface portion inside the case and the needle fixing part so as to be penetrated by the at least one needle and forming therein a space allowing a predetermined refrigerant to flow therethrough, wherein the refrigerant chamber is provided with a refrigerant inlet portion on one side thereof and a refrigerant outlet portion on an opposite side thereof, wherein the refrigerant inlet portion and the refrigerant outlet portion are connected to an external refrigerant supply unit such that the refrigerant cools the at least one needle penetrating the refrigerant chamber while flowing into the refrigerant chamber through the refrigerant inlet portion and flowing out to the refrigerant outlet portion according to an operation of the refrigerant supply unit.

2. The device according to claim 1, further comprising:

a heating portion provided to the contact surface portion to contact and heat the skin or an electrode portion provided to the contact surface portion and configured to generate heat by transmitting high-frequency energy to the contacted skin.

3. The device according to claim 2, further comprising:

a temperature sensor provided to the contact surface portion to sense a temperature of the contacted skin, wherein the heat generated by the heating portion or the high-frequency energy applied to the electrode portion is controlled according to the temperature sensed by the temperature sensor.

* * * * *